(12) United States Patent
Zhang et al.

(10) Patent No.: US 10,918,358 B2
(45) Date of Patent: Feb. 16, 2021

(54) MONITORING SYSTEM METHOD AND DEVICE

(71) Applicant: SHENZHEN MINDRAY BIO-MEDICAL ELECTRONICS CO., LTD., Shenzhen (CN)

(72) Inventors: Xiaocui Zhang, Shenzhen (CN); Yi Han, Shenzhen (CN); Shuo Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 477 days.

(21) Appl. No.: 15/863,363

(22) Filed: Jan. 5, 2018

(65) Prior Publication Data
US 2019/0125311 A1 May 2, 2019

Related U.S. Application Data

(63) Continuation of application No. PCT/CN2015/083766, filed on Jul. 10, 2015.

(51) Int. Cl.
*A61B 5/05* (2021.01)
*A61B 5/044* (2006.01)
(Continued)

(52) U.S. Cl.
CPC .......... *A61B 8/5261* (2013.01); *A61B 5/0402* (2013.01); *A61B 5/044* (2013.01);
(Continued)

(58) Field of Classification Search
CPC ....... A61B 8/5261; A61B 8/00; A61B 5/0402; A61B 5/04012; A61B 5/044;
(Continued)

(56) References Cited

U.S. PATENT DOCUMENTS

| 7,175,598 B2 | 2/2007 | Yoneyama |
| 2003/0045796 A1 | 3/2003 | Friedman |

(Continued)

FOREIGN PATENT DOCUMENTS

| CN | 1486675 | 4/2004 |
| CN | 1989910 | 7/2007 |

(Continued)

OTHER PUBLICATIONS

Chen, "Cardiac and vascular ultrasound biomechanics," Shanghai Science and Technology Education Press, Mar. 2014, Shanghai, pp. 84-86.

*Primary Examiner* — Amelie R Davis
*Assistant Examiner* — Adil Partap S Virk
(74) *Attorney, Agent, or Firm* — Kory D. Christensen

(57) ABSTRACT

A monitoring system comprises an ultrasonic imaging, an electrocardiograph monitoring module, a data processing module, and an output module. The ultrasonic imaging module is used for obtaining an echocardiogram of heart; the data processing module serves to receive the echocardiogram and obtaining, according to the echocardiogram, mechanical motion identifiers of atriums and ventricles; the data processing module outputs in real-time the mechanical motion identifiers for atriums and ventricles, together with electrocardiogram information, to the output module in a comparative manner.

20 Claims, 7 Drawing Sheets

(51) Int. Cl.
  *A61B 8/14* (2006.01)
  *A61B 8/08* (2006.01)
  *A61B 8/00* (2006.01)
  *A61B 5/0402* (2006.01)
  *A61B 5/04* (2006.01)
  *A61B 5/00* (2006.01)

(52) U.S. Cl.
  CPC ............ *A61B 5/04012* (2013.01); *A61B 8/00* (2013.01); *A61B 8/0883* (2013.01); *A61B 8/14* (2013.01); *A61B 8/463* (2013.01); *A61B 8/468* (2013.01); *A61B 8/5207* (2013.01); *A61B 8/5223* (2013.01); *A61B 5/7285* (2013.01); *A61B 8/486* (2013.01); *A61B 8/5284* (2013.01); *A61B 8/543* (2013.01)

(58) Field of Classification Search
  CPC ......... A61B 8/0883; A61B 8/14; A61B 8/463; A61B 8/468; A61B 8/5207; A61B 8/5223; A61B 5/7285; A61B 8/5284; A61B 8/543; A61B 8/486; G16H 50/30
  See application file for complete search history.

(56) References Cited

U.S. PATENT DOCUMENTS

| | | | |
|---|---|---|---|
| 2004/0044283 A1* | 3/2004 | Yoneyama | A61B 8/488 600/437 |
| 2004/0215077 A1* | 10/2004 | Witt | G01S 7/52088 600/443 |
| 2007/0167777 A1 | 7/2007 | Abe | |
| 2007/0167809 A1* | 7/2007 | Dala-Krishna | A61B 8/06 600/459 |
| 2008/0077012 A1 | 3/2008 | Gunji | |
| 2012/0165674 A1* | 6/2012 | Abe | A61B 8/0883 600/443 |
| 2015/0018632 A1* | 1/2015 | Khair | A61B 5/029 600/301 |
| 2015/0018684 A1 | 1/2015 | Abe | |
| 2015/0065814 A1* | 3/2015 | Kapoor | A61B 5/0022 600/301 |

FOREIGN PATENT DOCUMENTS

| | | |
|---|---|---|
| CN | 101147687 | 3/2008 |
| CN | 102821680 | 12/2012 |
| CN | 103429164 | 12/2013 |
| JP | H03191951 | 8/1991 |

* cited by examiner

MONITORING SYSTEM METHOD AND DEVICE

TECHNICAL FIELD

The present disclosure relates to medical devices, and more particularly to a monitoring system used for monitoring a periodic heart movement.

BACKGROUND

Generally, ECG monitoring devices are used to monitor the periodic movement of the heart, and diseases of patients are diagnosed based on the ECG, such as arrhythmia, ventricular capture and electrical mechanical dissociation. However, problems exist with current approaches.

Inaccuracies occur in monitoring arrhythmia by ECG monitoring. For example, when an atrial fibrillation occurs in the patient, interferences generated by clutters, resistance, or body position changes may exist, which decease accuracy in ECG monitoring.

In some special cases, such as external pacing, determination of the ventricular capture relying only on ECG will be inaccurate. Since the voltage level of the ECG signal of the external pacing is unstable, the QRS waves with low voltage will be prone to be missed. When the voltage is too high, overperception will occur. For example, appearance of a high T wave may lead to the determined heart rate to double. In addition, some pacing waves are very near to following waves. As a result, the following waves may be mistaken for QRS waves generated by ventricular capture (as shown in FIG. 1). In FIG. 1, the signals indicated by the black markers are pacing signals, and the following signals are not QRS waves generated by ventricular capture. However, because the pacing signals are very close to following signals, the following signals are frequently mistaken for a QRS wave group generated by ventricular capture, thereby leading to misdetermination of ventricular capture. Therefore, the ventricular capture cannot be accurately determined by ECG.

In addition, in clinical settings, electrical mechanical dissociation (EMD) is determined with reference to the patient's vital signs (e.g., no heart sound, pulse, respiration and blood pressure, etc) and ECG performance (e.g., sinus, regular, time periods in which P-QRS-T successively occur or shape of ECG with normal voltage). The electrical activities of the patient's heart may be directly displayed by the ECG, while the mechanical activities of the heart of the patient are indirectly represented through the patient's vital signs. For example, the pulse, respiration and blood pressure may be monitored in real time by patient monitor, and the heart sound may be determined through auscultation by the doctor. A determination based on these methods indirectly representing the mechanical activities of the heart may lead to a delay in an EMD diagnosis.

SUMMARY

In one embodiment, a monitoring system is provided, which may include an ultrasound imaging unit, an ECG monitoring unit, a data processing unit and an output unit. The ultrasound imaging unit may include: a probe which may transmit ultrasound waves to a tissue and receive ultrasound echoes which are reflected from the tissue and carry information about the tissue, where the tissue comprises a heart; and an image processing unit whose input is connected with the probe and which receives ultrasound echo signals outputted by the probe and processes the ultrasound echo signals to generate ultrasound images, wherein the ultrasound images comprises echocardiography images representing heart information.

The ECG monitoring unit may monitor ECG to generate ECG information over time. The input of the data processing unit may be connected with the output of the image processing unit and the output of the ECG monitoring unit. The data processing unit may receive the echocardiography images and generate mechanical movement markers of the atrium and the ventricle and output the mechanical movement markers of the atrium and the ventricle and the ECG information to the output unit for displaying.

In one embodiment, a method for monitoring the periodic movement of the heart is provided. The method may include: receiving ultrasound echoes which are reflected from the heart and carry information about the heart; generating echocardiography images according to the ultrasound echoes; generating mechanical movement markers of an atrium and a ventricle according to the echocardiography images; receiving ECG information which varies over time and is outputted by a ECG monitoring unit; and displaying the mechanical movement markers of the atrium and the ventricle and the ECG information.

In one embodiment, a device for monitoring the periodic movement of the heart is provided. The device may include: a probe which transmits ultrasound signals to a heart and receives ultrasound echoes that are reflected from the heart and carry information about the heart; an ECG monitoring unit which receives ECG information that varies over time; an image processing unit which receives the ultrasound echoes collected by the probe and generates echocardiography images according to the ultrasound echoes; and a data processing unit coupled to the ECG monitoring unit and the imaging processing unit that receives ECG information and electrocardiography images and generates mechanical movement markers of an atrium and a ventricle according to the echocardiography images and outputs the mechanical movement markers of the atrium and the ventricle and the ECG information to an output unit.

DETAILED DESCRIPTION

The concepts of the present disclosure may include detecting the mechanical activities of the heart using ultrasound monitoring, obtaining ECG signals using ECG monitoring and comparatively analyzing the mechanical activities of the heart and the ECG signals to represent the electrical mechanical activities of the heart in an intuitive way. The embodiments of the present disclosure will be described in detail below with reference to the drawings.

Figure 1:
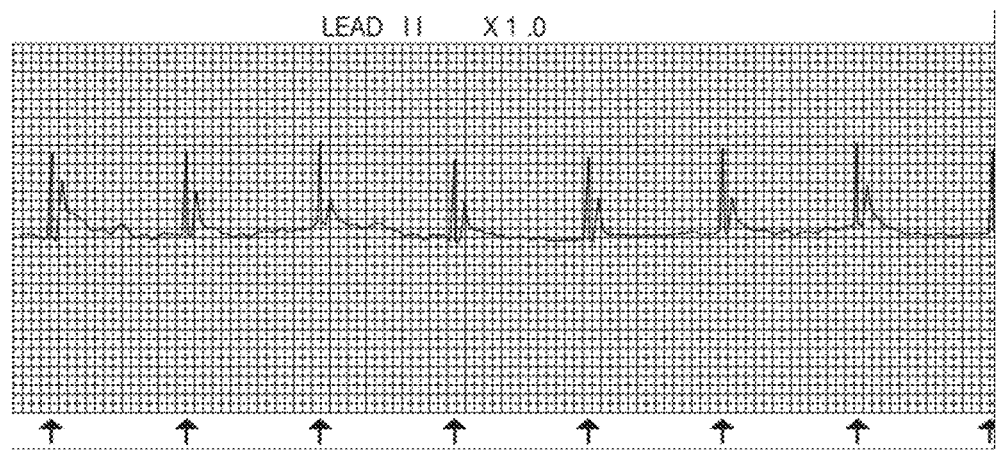
FIG. 1 is an ECG with external pacing.
Figure 2:
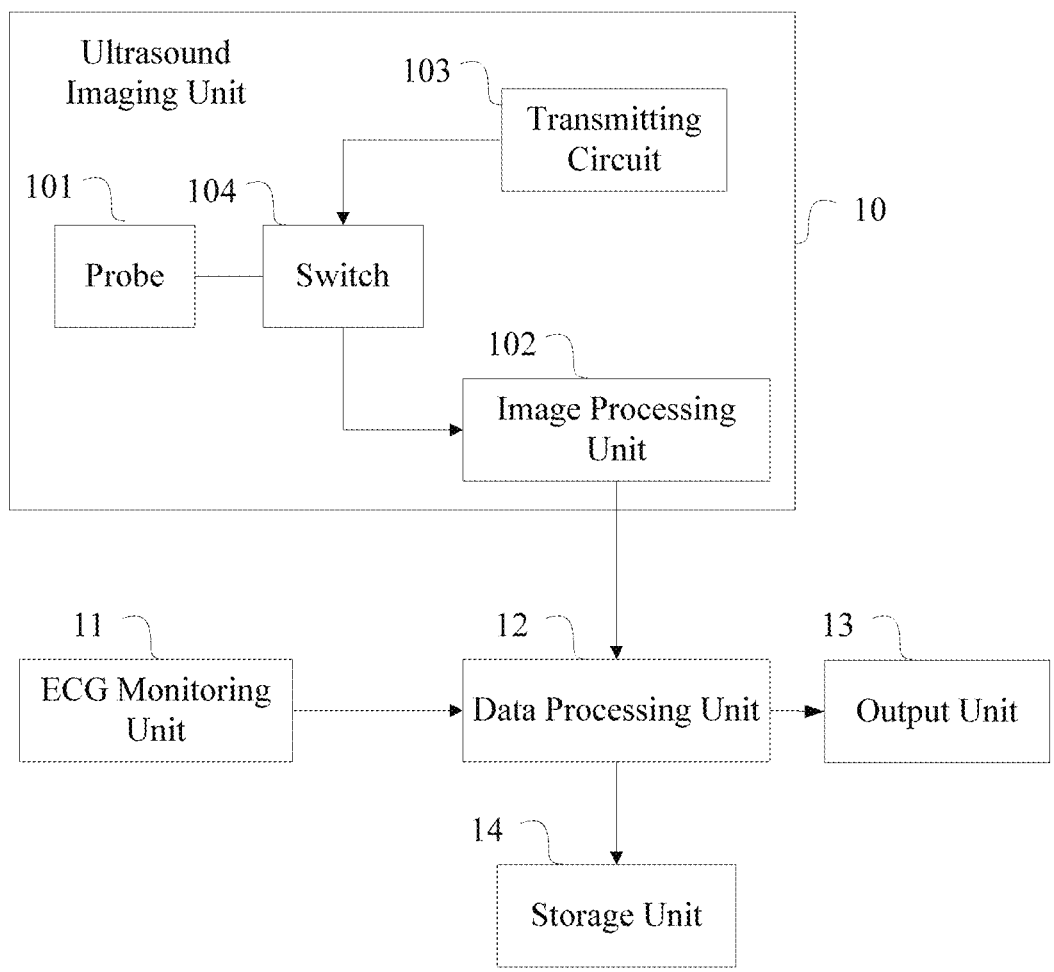
FIG. 2 is a schematic block diagram of a monitoring system in one embodiment.

Referring to FIG. 2, a monitoring system may include an ultrasound imaging unit 10, an ECG monitoring unit 11, a data processing unit 12 and an output unit 13. The ultrasound imaging unit 10 may include a probe 101, an image processing unit 102 and a transmitting circuit 103. The transmitting circuit 103 may be connected with the probe 101. An input of the image processing unit 102 may be connected with the probe 101. An input of the data processing unit 12 may be connected with an output of the image processing unit 102 and an output of the ECG monitoring unit 11. An output of the data processing unit 12 may be connected with the output unit 13. The connection here may be direct connection or indirect connection through intermediate device, and may be wireless or wired connection.

The probe 101 may be used to scan a tissue to be inspected, which may transmit ultrasound waves to the tissue to be inspected and receive ultrasound echoes reflected from the tissue and carrying information about the tissue. Based on actual needs, various suitable probes may be used. The probe 101, in one embodiment, may be coupled to the transmitting circuit 103 through a switch 104 and transmit the ultrasound waves to the tissue to be inspected under the control of the transmitting circuit 103. The probe 101 may send received ultrasound echo signals to the image processing unit 102 via the switch 104. In one embodiment, the probe 101 may transmit ultrasound waves to a heart and receive ultrasound echoes reflected from the heart tissue and carrying information about the heart tissue. In one embodiment, the probe may monitor the heart continuously. In order to facilitate the continuous monitoring, the probe may have structure and/or shape suitable for being affixed on the body surface of the object to be inspected for long period of time.

The transmitting circuit 103 may generate a transmission logic sequence based on needs and output the transmission logic sequence to the probe 101. The probe 101 may generate ultrasound waves based on the transmission logic sequence. In one embodiment, the transmitting circuit 103 may further control the probe to scan the tissue to be inspected continuously in a pre-set time period. In one embodiment, in order to avoid the temperature increase of the probe caused by the continuous scan, the transmitting circuit 103 may also control the probe to stop scanning for a time period after every continuous monitoring in a pre-set time period is completed. The time interval between the scans and the duration of the scan cycle may be set by the doctor. For example, the scan may start once every five minutes, and the duration of each scan may be one minute.

The image processing unit 102 may process the ultrasound echoes, such as beam forming, demodulation, and image processing, etc., and generate ultrasound images according to desired ultrasound image mode. In one embodiment, the ultrasound images may be various echocardiography images. The image processing unit 102 may be an integrated circuit. Alternatively, the image processing unit 102 may be circuit formed by discrete components. In one embodiment, the image processing unit 102 may be a processor.

The ECG monitoring unit 11 generally may include multiple leads and a processing circuit. The leads may be contacted with the surface of the body to be inspected near the heart and sense the electric signals conducted by the chambers of the heart. The processing circuit may process the electric signals, such as amplification, filtering or A/D conversion, etc., and output the processed ECG information to the data processing unit 12.

The data processing unit 12 may process the various data, and may also send control signals to the components of the monitoring system to control the components. The data processing unit 12 may also store the data to and/or read the data from a storage unit 14, and may output the data to the output unit 13 where the data may be displayed. In one embodiment, the input of the data processing unit 12 may be connected with the output of the image processing unit 102 and the output of the ECG monitoring unit 11 and may receive the echocardiography images outputted by the image processing unit 102 and the ECG information outputted by the ECG monitoring unit 11. The data processing unit 12 may detect the mechanical movements of the atrium and the ventricle based on the echocardiography images, mark the time period during which the mechanical movements occur to obtain mechanical movement markers of the atrium and the ventricle, and output the mechanical movement markers of the atrium and the ventricle and the ECG information to the output unit 13 where they may be displayed or presented for observation by the inspectors or doctors.

In one embodiment, the mechanical movement markers of the atrium and the ventricle and the ECG information may be outputted to the output unit 13 for displaying or presenting in real time, so as to, for example, monitor the object to be monitored in real time. In another embodiment, the mechanical movement markers of the atrium and the ventricle and the ECG information may be outputted to the output unit 13 for displaying or presenting in non-real-time manner. For example, the mechanical movement markers of the atrium and the ventricle and the ECG information may be previously stored in the monitoring system, and thereafter may be outputted to the output unit 13 when needed so as to facilitate the subsequent, off-line or off-site observation and analysis by the doctor of the object monitored.

In one embodiment, the mechanical movement markers of the atrium and the ventricle and the ECG information may be outputted to the output unit 13 and displayed or presented thereon in a comparative manner. The comparative manner may include comparison in visual, audio or combination thereof. The visual comparison may include image comparison and light signal comparison. The audio comparison may include sound comparison. For example, the mechanical movement markers of the atrium or the ventricle and the ECG information may be processed into visual images or flashing light signals with set colors. Alternatively, the mechanical movement markers of the atrium or the ventricle and the ECG information may be processed into sound signals. Since the echocardiography images and the ECG information have time consistency during the acquisition and processing thereof, the mechanical movement markers of the atrium or the ventricle and the ECG waves of the ECG information may be compared in time. The data processing unit 12 may be integrated circuit. Alternatively, the data processing unit 12 may be circuit formed by discrete components. In one embodiment, the data processing unit 12 may be a microprocessor. In one embodiment, the data processing unit 12 and the image processing unit 102 may be separate unit, or alternatively be integrated in a single unit. Likewise, some functions of the data processing unit 12 may be implemented in the image processing unit 102 or vice versa.

The output unit 13 may be used to present the signals outputted by the data processing unit 12. The output unit 13 may be a display device, a light emission unit, or a speaker. In the case that the display device is used as the output unit 13, the data processing unit may process the mechanical movement markers into visual markers and process the ECG information into electrocardiogram and display the mechanical movement markers of the atrium or the ventricle and the ECG information on the display device along the same timeline in real time. In the case that the light emission unit or the speaker is used as the output unit 13, the data processing unit 12 may process the mechanical movement markers into light signals or sound signals, process the ECG information into light signals or sound signals, and output the mechanical movement markers of the atrium or the ventricle and the ECG information to the light emission unit or the speaker along the same timeline in real time. The light emission unit may emit lights based on the light signals. The speaker may play the sound based on the sound signals. The mechanical movements of the atrium or the ventricle and the ECG information may be distinguished based on the colors of the lights or the different sounds.

Figure 3:
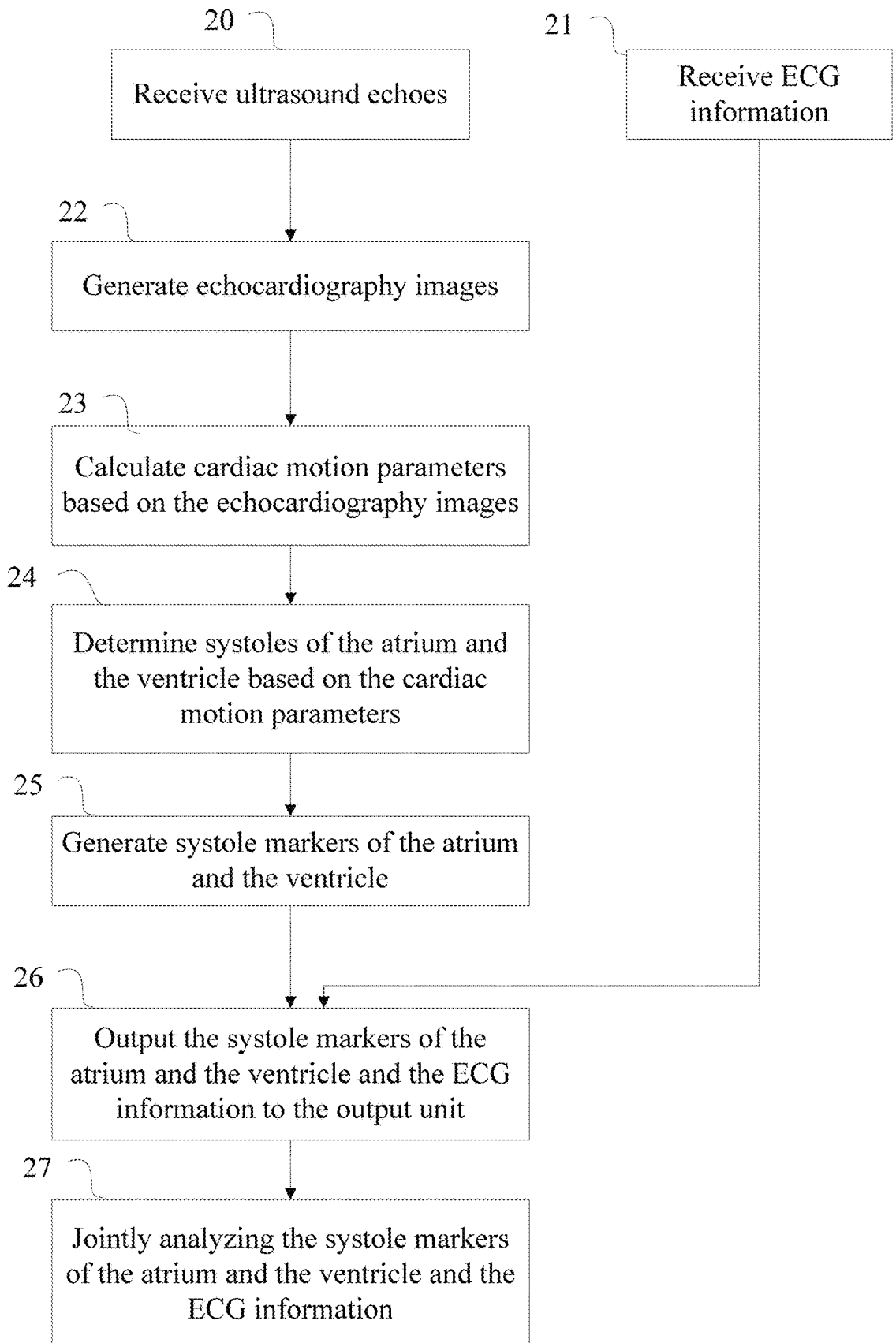
FIG. 3 is a schematic flow chart for monitoring the periodic movement of the heart in one embodiment.

When monitoring the periodic movement of the heart using the monitoring system above, one monitoring method is as shown in FIG. 3, which may include the following steps.

In step 20, the ultrasound echoes reflected from the heart of the object inspected and carrying information about the heart may be received by the probe. In one embodiment, the probe may be affixed on the body surface of the patient for a long period of time to perform an intermittent long-time monitoring, i.e., the continuous transmitting of ultrasound waves and receiving of echoes for a time period may be performed every certain time period.

In step 21, the ECG information varying over time outputted by the ECG monitoring unit may be received.

In step 22, the echocardiography images may be generated based on the ultrasound echoes. In one embodiment, the echocardiography images may be M mode ultrasound images. In other embodiments, the echocardiography images may be two-dimensional ultrasound images or contrast ultrasound images, etc. In one embodiment, the type of the echocardiography images may be selectable. For example, the echocardiography images may be a default type. Thereafter, it may be possible for the user to change the type of the echocardiography images. After the user select the type, the selected type of echocardiography images may be generated.

In step 23, cardiac motion parameters may be calculated based on the echocardiography images. The cardiac motion parameters may include atrial end-diastolic time point, ventricular end-diastolic time point, atrial end-systolic time point, ventricular end-systolic time point, atrial diastolic duration, ventricular diastolic duration, atrial systolic duration, ventricular systolic duration, atrial end-diastolic inner diameter, ventricular end-diastolic inner diameter, atrial end-systolic inner diameter and ventricular end-systolic inner diameter. Before calculating the cardiac motion parameters, the mode of the echocardiography images may be determined and the features in the echocardiography images may be extracted based on the mode, such as left ventricular posterior wall, ventricular septum, left atrial cavity wall or the like. These features may be used to calculate the cardiac motion parameters.

Figure 4:
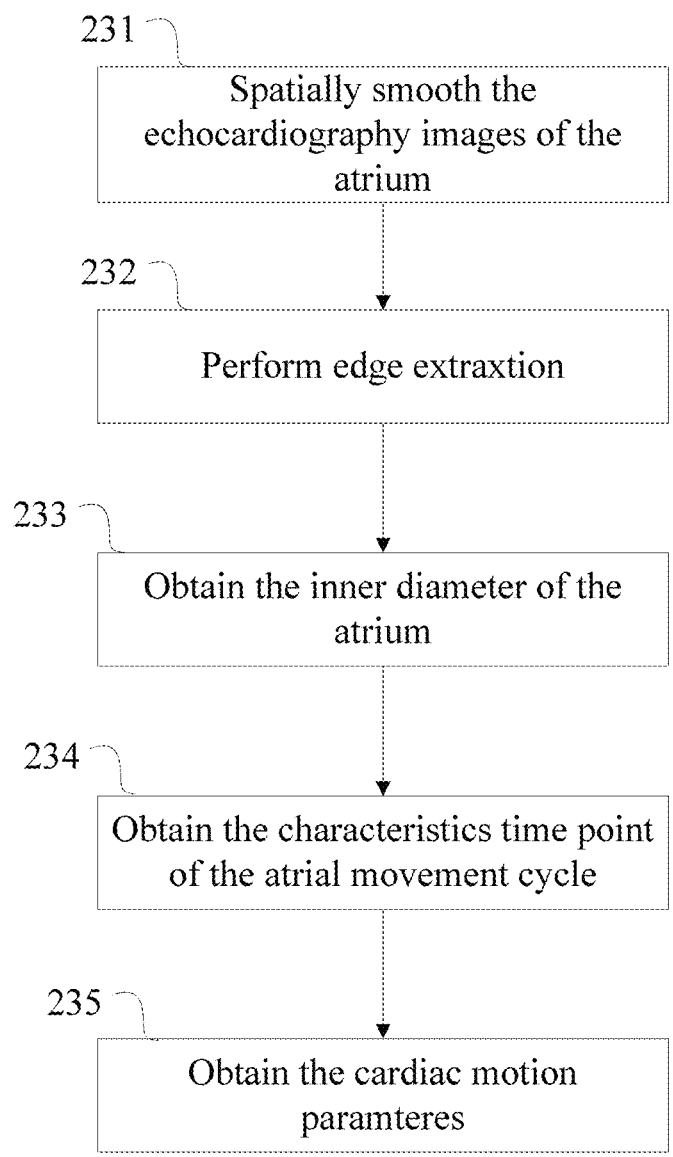
FIG. 4 is a schematic flow chart for calculating the cardiac motion parameters in one embodiment.

Taking the M mode echocardiography images (which may also be referred to as M images) of left atrium as an example, one method for calculating the cardiac motion parameters may be as shown in FIG. 4, which may include the following steps.

In step 231, the M mode echocardiography images of the left atrium may be spatially smoothed so as to eliminate the noise interference.

Figure 5:
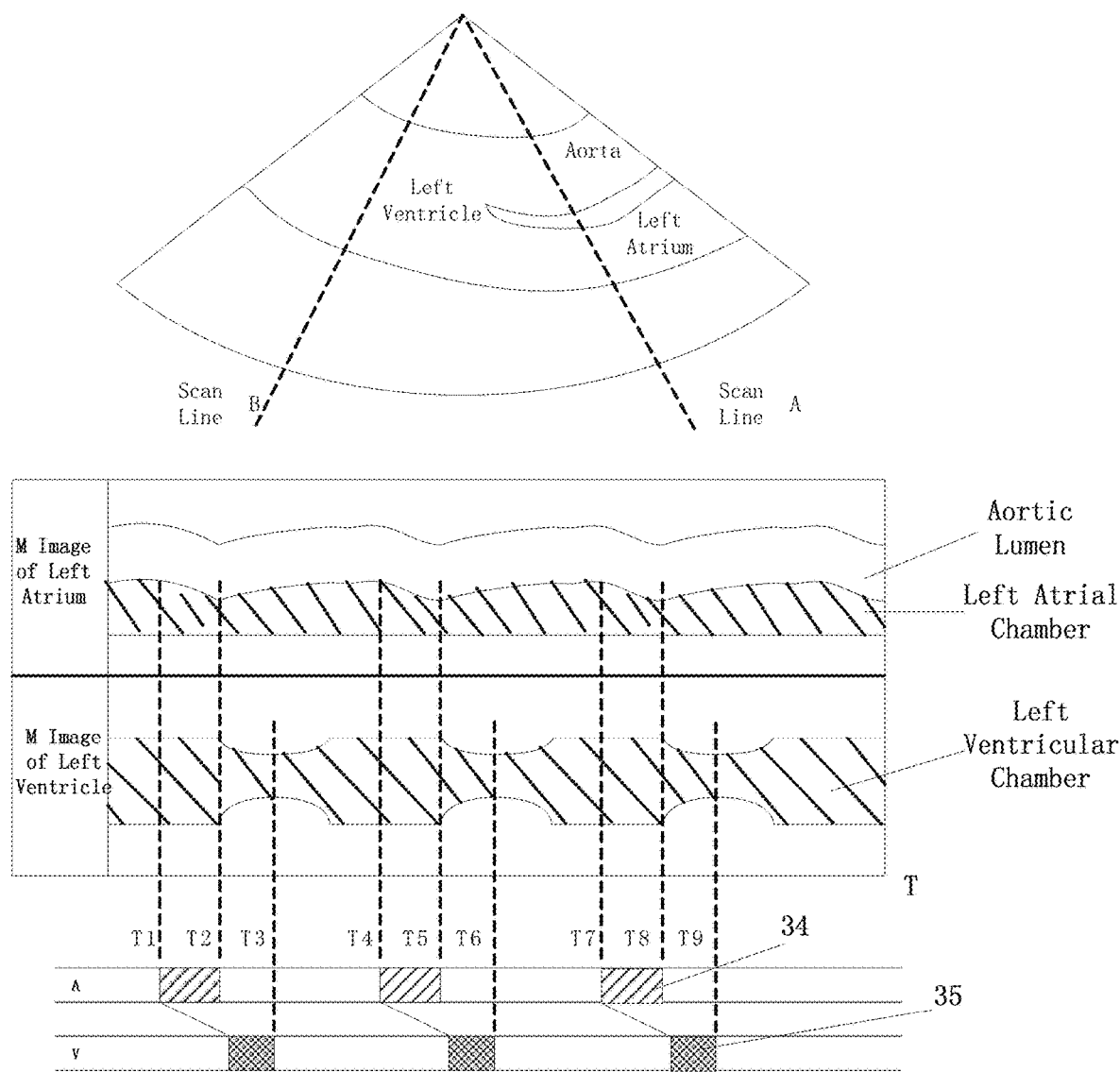
FIG. 5 schematically shows the systoles of the atrium and the ventricle and the three-row graph.
Figure 6:
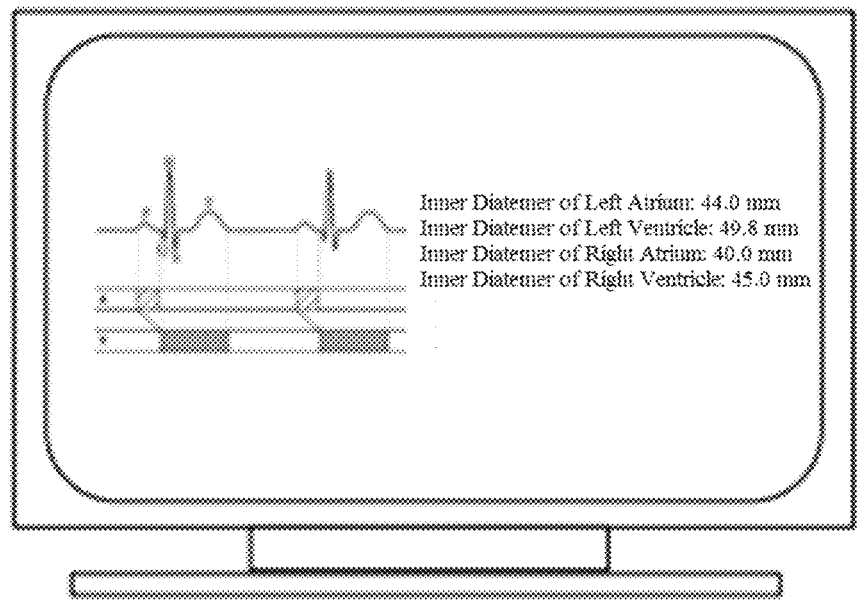
FIG. 6 schematically shows the comparative analysis of the systoles of the atrium and the ventricle and the ECG in the first manner.

In step 232, edge extraction may be performed on the smoothed images to identify the left atrial chamber. The trajectories of the edges of the aortic lumen and the left atrial chamber may be obtained by the edge extraction, as shown in FIG. 5. Therefore, the left atrial chamber may be identified based on the relative positions of the aortic lumen and the left atrial chamber. As shown in FIG. 5, the chamber region whose ordinates are at the bottom may represent the left atrial chamber 31 while the chamber region whose ordinates are at the top may represent the aortic lumen 32.

In step 233, the inner diameter of the left atrial chamber may be obtained according to the trajectories of the edges of the left atrial chamber. The inner diameter of the left atrial chamber may be the longitudinal distance between the upper and lower edges of the left atrial chamber.

In step 234, characteristics time points of the atrial movement cycle may be obtained by comparing the inner diameters of the left atrial chamber at the various time points. The characteristics time points of the atrial movement cycle may include an atrial end-diastolic time point and an atrial end-systolic time point. The atrial end-diastolic time point may be the time point where the inner diameter of the atrium is the largest, such as T1\T4\T7 in FIG. 5. The atrial end-systolic time point may be the time point where the inner diameter of the atrium is the smallest, such as T2\T5\T8 in FIG. 5.

In step 235, the cardiac motion parameters may be obtained based on the characteristics time points of the atrial movement cycle. As shown in FIG. 5, the motion parameters of the atrium may be obtained according to the characteristics time points of the atrial movement cycle. In FIG. 5, the time points T1\T4\T7 are the atrial end-diastolic time points, the time points T2\T5\T8 are the atrial end-systolic time points, the time period between an atrial end-diastolic time point and the atrial end-systolic time point closely following this atrial end-diastolic time point is the atrial systolic duration, the time period between an atrial end-systolic time point and the atrial end-diastolic time point closely following this atrial end-systolic time point is the atrial diastolic duration, the inner diameter of the atrium at the atrial end-diastolic time point is the atrial end-diastolic inner diameter, and the inner diameter of the atrium at the atrial end-systolic time point is the atrial end-systolic inner diameter.

Similarly, the M images of the left ventricle may be spatially smoothed so as to eliminate the noise interference. The trajectories of the edge of the left ventricular chamber 33 may be obtained through edge extraction, as shown in FIG. 5. The inner diameter, i.e., the longitudinal distance between the upper and lower edges of the left ventricular chamber, may be obtained. The characteristics time points of the ventricular movement cycle may be obtained, where the characteristics time points of the ventricular movement cycle may include ventricular end-diastolic time point and ventricular end-systolic time point. The ventricular end-diastolic time point may be the time point where the inner diameter of the ventricle is the largest and begin to become smaller, such as T2\T5\T8 in FIG. 5. The ventricular end-systolic time point may be the time point where the inner diameter of the ventricle is the smallest, such as T3\T6\T9 in FIG. 5. Similarly, the motion parameters of the ventricle may be obtained based on the characteristics time points of the ventricular movement cycle. In FIG. 5, the time points T2\T5\T8 are the ventricular end-diastolic time points, the time points T3\T6\T9 are the ventricular end-systolic time points, the time period between an ventricular end-diastolic time point and the ventricular end-systolic time point closely following this ventricular end-diastolic time point is the ventricular systolic duration, the time period between an ventricular end-systolic time point and the ventricular end-diastolic time point closely following this ventricular end-systolic time point is the ventricular diastolic duration, the inner diameter of the ventricle at the ventricular end-diastolic time point is the ventricular end-diastolic inner diameter, and the inner diameter of the ventricle at the ventricular end-systolic time point is the ventricular end-systolic inner diameter.

In step 24, the systoles of the atrium and the ventricle may be determined based on the motion parameters of the heart. The systole of the atrium may be obtained based on the atrial end-diastolic time point, the atrial end-systolic time point and the atrial systolic duration, and the systole of the ventricle may be obtained based on the ventricular end-diastolic time point, the ventricular end-systolic time point and the ventricular systolic duration.

In step 25, the mechanical movement markers corresponding to the systoles of the atrium and the ventricle may be generated. In one embodiment, the mechanical movement markers corresponding to the systole of the atrium and the ventricle may be visual markers. For example, a column chart may be used to represent the systoles of the atrium and the ventricle, where the length of the columns in the column chart represent the systolic duration of the chamber corresponding to the column chart. The mechanical movement markers may be presented using a graph similar to "three-row graph" below. As shown in FIG. 5, horizontal column charts may be used to represent the systoles of the atrium and the ventricle. The column chart 34 located at the first row and filled with slashes may represent the systole of the atrium, while the column chart 35 located at the third row and filled with dots may represent the systole of the ventricle. In the present embodiment, the length directions of the column chart 34 and 35 are parallel to the time axis T. Two ends of the column chart 34 respectively correspond to atrial end-diastolic time point T1\T4\T7 and atrial end-systolic time point T2\T5\T8, and the length of the column chart 34 represents the atrial systolic duration. Two ends of the column chart 35 respectively correspond to ventricular end-diastolic time point T2\T5\T8 and ventricular end-systolic time point T3\T6\T9, and the length of the column chart 35 represents the ventricular systolic duration. A distance may be formed between the column charts representing the atrial systole and the ventricular systole in a direction perpendicular to the time axis, which form the second row between the first row and the third row. Connection lines located in the second row may connect the end-diastolic time points of two column charts. The connection lines represent consecutive conduction, and also represent atrioventricular period between the systole of the atrium and the ventricle. The steeper the connection line, the shorter the time from the atrium to the ventricle, the faster the heart beats. In the present embodiments, the three-row graph can represent not only the information about consecutive conduction, but also the information about the time of the systole of the atrium and the ventricle.

In step 26, the systole markers of the atrium and the ventricle and the ECG information may be outputted to the output unit to be comparatively displayed in real time. As shown in FIGS. 6 to 9, the data processing unit may output the systole markers of the atrium and the ventricle and the ECG information to the display device to be displayed in the same timeline in real time.

In step 27, the systole markers of the atrium and the ventricle and the ECG information may be analyzed jointly. The analysis may be done by the doctor. The doctor can determine whether the electrical signals of the atrium and the ventricle (P wave and QRS wave) detected in the ECG are followed by mechanical activities of corresponding chamber by the displayed graphs. Therefore, the doctor can make the determination in a more direct and intuitive way, and the misdetermination due to lack of experience may be avoided.

Figure 7:
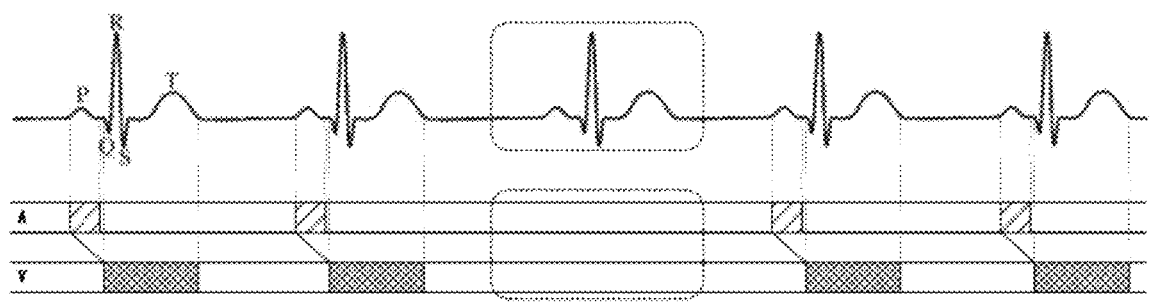
FIG. 7 schematically shows the comparative analysis of the systoles of the atrium and the ventricle and the ECG in the second manner.
Figure 8:
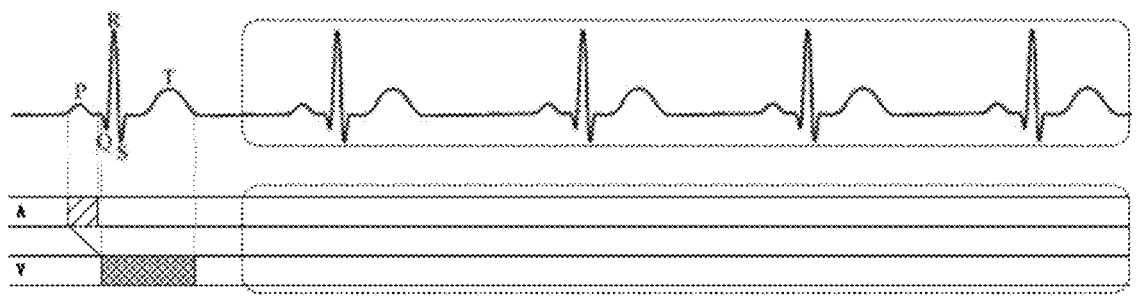
FIG. 8 schematically shows the comparative analysis of the systoles of the atrium and the ventricle and the ECG in the third manner.
Figure 9:
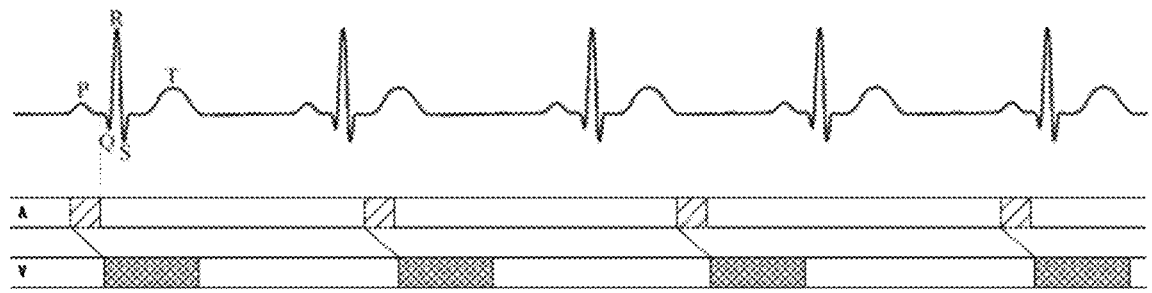
FIG. 9 schematically shows the comparative analysis of the systoles of the atrium and the ventricle and the ECG in the fourth manner.
Figure 10:
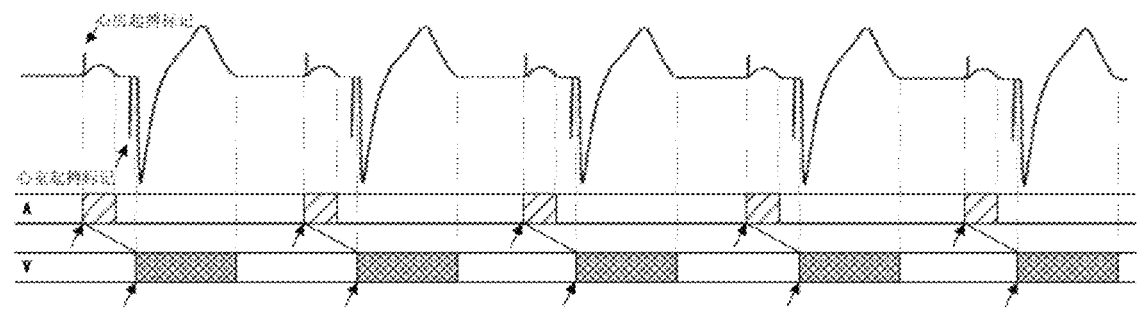
FIG. 10 schematically shows an analysis graph in which the real-time data of the inner diameter of the heart chamber is added.

The analysis may also be automatically achieved by the monitoring system. The data processing unit may determine whether the P wave and the QRS wave in the ECG information is consistent with the systole markers of corresponding chamber in rhythm and frequency. i.e., whether the atrial systole marker appears at the same time when the P wave appears and whether the ventricular systole marker appears at the same time when the QRS wave appears. When it is determined that they are not consistent in rhythm and frequency, the data processing unit may output alarm information. The automatic analysis may eliminate the need for the doctors to make the determination, and may directly obtain the determination and alarm based on the result of the determination. For example, when mismatch of electric-mechanical activities is detected, the monitoring system may alarm correspondingly. For example, in the case that a certain electric signal is detected in the ECG while no mechanical activity is detected in the echocardiography images, as shown in FIG. 7 in which ECG signals are detected in the dotted box in the ECG while no mechanical pulsation is detected in the echocardiography, it may be determined that the ECG signals failed to evoke a valid heart beat and a heart-block occurred. In the case that the ECG signals are detected in the ECG while no mechanical activity is detected in the echocardiography image, as shown in FIG. 8 in which the ECG signals are successively detected in the dotted box in the ECG while the echocardiography image shows that the heart is in a state of stopping beating, it may be determined that mechanical arrest occurred. In the case that the heart rate detected by the ECG is faster than the frequency of the mechanical activity detected by the echocardiography image, as shown in FIG. 9 in which 5 ECG signals are detected in the ECG while only 4 mechanical signals are detected by the echocardiography image and the mechanical signals and the ECG signals have respective frequency, it may be determined that frequency separation occurred. When arrhythmia or special circumstance occurs, the features described above may be used to confirm the diagnostic results obtained by ECG in a more intuitive manner, thereby ensuring the accuracy and rationality of the diagnosis. In the case of external pacing, the features described above may be used to determine the ventricular capture more accurately. As shown in FIG. 10, since the three-row graph shows that each pacing wave is followed by a valid QRS wave group, it may be determined that the heart was ventricular-captured.

In order to show the changes of the inner diameters o the heart chambers in more detail, the real-time inner diameters of the heart chambers may be further displayed near the three-row graph.

In the present embodiment, the ultrasound monitoring is used to directly represent the mechanical activities of the heart, which is more direct, more intuitive and more timely compared with the solutions in which patient's signs (e.g., no heart sound, pulse, respiration and blood pressure, etc) are used to indirectly represent the mechanical activities of the heart. Furthermore, the mechanical activities of the heart may be represented by markers and comparatively displayed with the ECG data obtained by ECG monitoring, thereby determining the mismatch of the electric-mechanical activities. This way, the determination is more intuitive, and the reliance on professional skills and experiences of the doctor is reduced. Therefore, the determination of the states of the periodic movement of the heart may be easier and more accurate.

In the present embodiment, the mechanical movement markers may be the systole markers of the chambers of the heart, including the atrial systole marker and the ventricular systole marker. In other embodiments, the mechanical movement markers may be diastole marker of the chambers of the heart, including atrial diastole marker and ventricular diastole marker.

Figure 11:
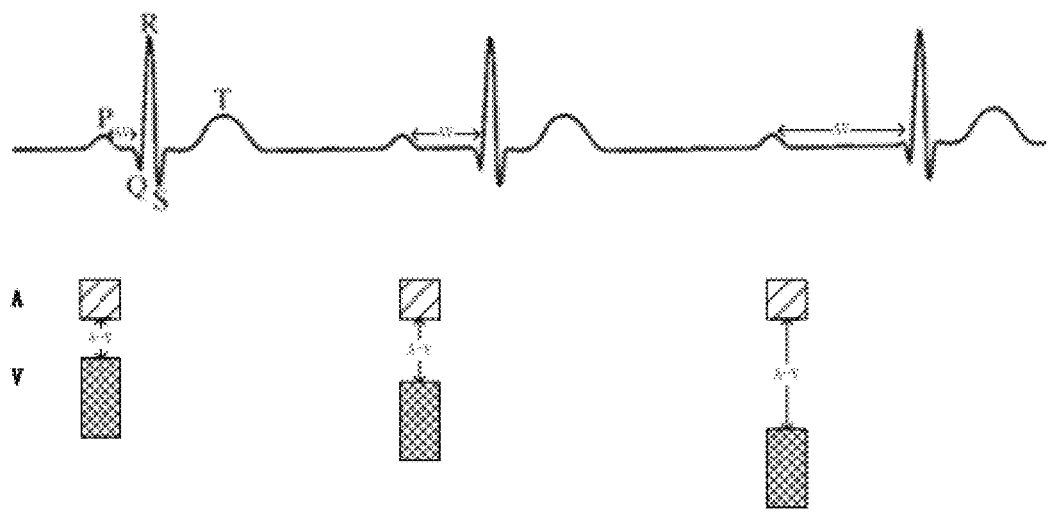
FIG. 11 is a schematic graph in which upright column charts are used to represent the systoles of the atrium and the ventricle.

In other embodiments, other ways may also be used to intuitively represent the mechanical activities of the atrium and the ventricle and the conduction therebetween. For example, as shown in FIG. 11, upright column charts may be used to represent the systoles of the atrium and the ventricle. Two column charts may be displayed in the same column. The length direction of the column chart may be vertical to the time axis, and the length of the column of the column charts may represent the systolic duration of the chamber corresponding to the column chart. In the figure, the column charts A may represent the atrial systole markers and the column charts V may represent the ventricular systole markers. The distance A-V between the atrial systole marker and the ventricular systole marker in the direction perpendicular to the time axis may be related to atrioventricular conduction time. The larger the distance is, the slower the atrioventricular conduction will be. The smaller the distance is, the faster the atrioventricular conduction will be.

Figure 12:
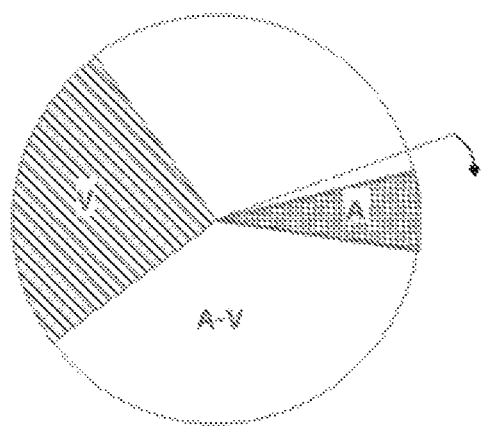
FIG. 12 is a schematic graph in which a pie chart is used to represent the mechanical movements of the atrium and the ventricle.

As shown in FIG. 12, a pie chart may be used to represent the mechanical activities of the atrium and the ventricle. The pie chart may be updated around the center over time. Updating one cycle may represent one heart cycle, and the atrial systole information, the atrioventricular period information and the ventricular systole information may be successively updated. In the figure, the sector A may represent the atrial systole marker and the sector V may represent the ventricular systole marker. The magnitude of the angle of the sectors may represent the length of the time. A-V may represent the atrioventricular conduction.

Figure 13:
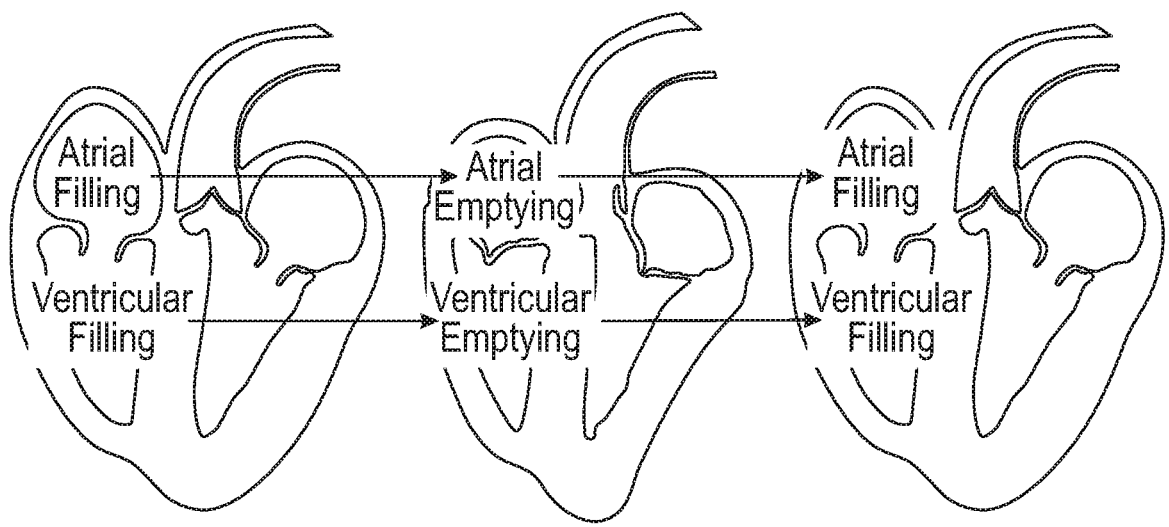
FIG. 13 is a schematic graph in which schematic views of heart are used to represent the mechanical movement of the heart.

As shown in FIG. 13, schematic views which show the systolic process may be used to represent the mechanical activities of the atrium and the ventricle. The systolic and diastolic processes may be reproduced according to the heart diameter information obtained by the echocardiography images. This way, the mechanical activities of the heart may be presented to the user more intuitively.

Furthermore, sound may be used to represent the systole, diastole of the atrium and the ventricle and the atrioventricular period. For example, "toot" may be used to represent the mechanical activities of the heart and "beep" may be used to represent the ECG. Using the sound, medical personnel may identify the changes of the heart of the patient more intuitively. In addition, it is also possible that one of the mechanical activities and the ECG is represented by sound and the other is represented by images.

A person skilled in the art will understand that all or a part of the steps of the methods in the embodiments above may be implemented by programs executed by related hardware, such as a processor. The programs may be stored on a computer readable storage medium. The storage medium may include ROM, RAM, disk or disc, etc.

The present disclosure has been described with reference to specific embodiments. However, the description above is only used to facilitate understanding to, but not limit, the present disclosure. Modifications may be made to the specific embodiments based on the concepts of the present disclosure by a person ordinarily skilled in the art.

What is claimed is:

1. A monitoring system, comprising:
   an ultrasound imaging unit comprising:
      a probe which transmits ultrasound waves to a tissue and receives ultrasound echoes which are reflected from the tissue and carry information about the tissue, wherein the tissue comprises a heart; and
      an image processing unit input connected with the probe which receives ultrasound echo signals outputted by the probe and processes the ultrasound echo signals to generate ultrasound images, wherein the ultrasound images comprises echocardiography images representing heart information;
   an electrocardiogram (ECG) monitoring unit which monitors ECG to generate ECG information varying over time; and
   a data processing unit having an input connected with an output of the image processing unit and an output of the ECG monitoring unit, wherein the data processing unit receives the echocardiography images and generates mechanical movement markers of an atrium and a ventricle and outputs the mechanical movement markers of the atrium and the ventricle and the ECG information to an output unit,
   wherein the mechanical movement markers are systole markers of heart chambers which comprise atrial systole markers and ventricular systole markers;
   wherein the atrial systole markers and ventricular systole markers are graphically represented as bars that are displayed in a time relationship with the ECG information; and
   wherein a length of each atrial systole marker and ventricular systole marker indicates an atrial systolic duration and a ventricular systolic duration, respectively;
   wherein each bar is parallel to a time axis, each bar corresponding to an atrial systole is displayed in a first line parallel to the time axis, each bar corresponding to a ventricular systole is displayed in a second line parallel to the time axis, and two ends of each bar respectively correspond to an end-diastolic time point and an end-systolic time point;
   wherein a distance is formed between the bars representing the atrial systole and the ventricular systole of a heartbeat, and wherein a connection line is displayed connecting the end-diastolic time points of two bars.

2. The monitoring system of claim 1, wherein the data processing unit outputs the mechanical movement markers of the atrium and the ventricle and the ECG information to the output unit in a comparative manner.

3. The monitoring system of claim 1, wherein, the output unit comprises a display device, and the data processing unit displays the mechanical movement markers of the atrium and the ventricle and the ECG information on the display device along a same timeline.

4. The monitoring system of claim 1, wherein the data processing unit further determines whether electric signals of the atrium and the ventricle in the ECG information are consistent with the mechanical movement markers in rhythm and frequency and outputs alarm information in a case that they are not consistent.

5. The monitoring system of claim 1, wherein, the output unit comprises a speaker, the mechanical movement markers further include sound markers, and the data processing unit outputs sound signals corresponding to the ECG information and mechanical movement of the atrium and the ventricle to the speaker.

6. The monitoring system of claim 1, wherein, the ultrasound imaging unit further comprises a transmitting circuit, an output of the transmitting circuit is coupled to the probe, and the transmitting circuit generates a transmission logic sequence based on needs and controls the probe to scan the tissue continuously in a pre-set time period.

7. The monitoring system of claim 6, wherein the transmitting circuit controls the probe to stop scan for a time period after every continuous monitoring in a pre-set time period is completed.

8. The monitoring system of claim 1, wherein the data processing unit obtains trajectories of edges of the atrium and the ventricle according to the echocardiography images, obtains inner diameters of the atrium and the ventricle according to the trajectories of the edges of the atrium and the ventricle, obtains characteristics time points of movement cycles of the atrium and the ventricle according to the inner diameters, determines systoles of the atrium and the ventricle according to the characteristics time points of the movement cycles, and obtains the mechanical movement markers according to the systoles of the atrium and the ventricle.

9. The monitoring system of claim 8, wherein the echocardiography images are M mode ultrasound images.

10. The monitoring system of claim 1, wherein the data processing unit calculates cardiac motion parameters based on the echocardiography images, determines systoles of the atrium and the ventricle based on the cardiac motion parameters and generates the mechanical movement markers corresponding to the systoles of the atrium and the ventricle, and wherein the cardiac motion parameters comprises an atrial end-diastolic time point, a ventricular end-diastolic time point, an atrial end-systolic time point, a ventricular end-systolic time point, an atrial diastolic duration, a ventricular diastolic duration, an atrial systolic duration, a ventricular systolic duration, an atrial end-diastolic inner diameter, a ventricular end-diastolic inner diameter, an atrial end-systolic inner diameter and a ventricular end-systolic inner diameter.

11. A monitoring system, comprising:
an ultrasound imaging unit comprising:
a probe which transmits ultrasound waves to a tissue and receives ultrasound echoes which are reflected from the tissue and carry information about the tissue, wherein the tissue comprises a heart; and
an image processing unit input connected with the probe which receives ultrasound echo signals outputted by the probe and processes the ultrasound echo signals to generate ultrasound images, wherein the ultrasound images comprises echocardiography images representing heart information;
an electrocardiogram (ECG) monitoring unit which monitors ECG to generate ECG information varying over time; and
a data processing unit having an input connected with an output of the image processing unit and an output of the ECG monitoring unit, wherein the data processing unit receives the echocardiography images and generates mechanical movement markers of an atrium and a ventricle and outputs the mechanical movement markers of the atrium and the ventricle and the ECG information to an output unit,
wherein the mechanical movement markers are systole markers of heart chambers which comprise atrial systole markers and ventricular systole markers;
wherein the atrial systole markers and ventricular systole markers are graphically represented as bars that are displayed in a time relationship with the ECG information; and
wherein a length of each atrial systole marker and ventricular systole marker indicates an atrial systolic duration and a ventricular systolic duration, respectively;
wherein said bars are perpendicular to a time axis, two bars corresponding to an atrial systole and a ventricular systole of a heartbeat are displayed in a line perpendicular to the time axis, and a distance between the two bars indicates an atrioventricular conduction time.

12. The monitoring system of claim 11, wherein the data processing unit further determines whether electric signals of the atrium and the ventricle in the ECG information are consistent with the mechanical movement markers in rhythm and frequency and outputs alarm information in a case that they are not consistent.

13. The monitoring system of claim 11, wherein, the ultrasound imaging unit further comprises a transmitting circuit, an output of the transmitting circuit is coupled to the probe, and the transmitting circuit generates a transmission logic sequence based on needs and controls the probe to scan the tissue continuously in a pre-set time period.

14. The monitoring system of claim 13, wherein the transmitting circuit controls the probe to stop scan for a time period after every continuous monitoring in a pre-set time period is completed.

15. The monitoring system of claim 11, wherein the data processing unit obtains trajectories of edges of the atrium and the ventricle according to the echocardiography images, obtains inner diameters of the atrium and the ventricle according to the trajectories of the edges of the atrium and the ventricle, obtains characteristics time points of movement cycles of the atrium and the ventricle according to the inner diameters, determines systoles of the atrium and the ventricle according to the characteristics time points of the movement cycles, and obtains the mechanical movement markers according to the systoles of the atrium and the ventricle.

16. The monitoring system of claim 11, wherein the data processing unit calculates cardiac motion parameters based on the echocardiography images, determines systoles of the atrium and the ventricle based on the cardiac motion parameters and generates the mechanical movement markers corresponding to the systoles of the atrium and the ventricle, and wherein the cardiac motion parameters comprises an atrial end-diastolic time point, a ventricular end-diastolic time point, an atrial end-systolic time point, a ventricular end-systolic time point, an atrial diastolic duration, a ventricular diastolic duration, an atrial systolic duration, a ventricular systolic duration, an atrial end-diastolic inner diameter, a ventricular end-diastolic inner diameter, an atrial end-systolic inner diameter and a ventricular end-systolic inner diameter.

17. A method for monitoring a periodic movement of a heart, comprising:
   receiving ultrasound echoes which are reflected from the heart and carry information about the heart;
   generating echocardiography images according to the ultrasound echoes;
   generating mechanical movement markers of an atrium and a ventricle according to the echocardiography images;
   receiving electrocardiogram (ECG) information which varies over time and is outputted by a ECG monitoring unit; and
   displaying the mechanical movement markers of the atrium and the ventricle and the ECG information;
   wherein the mechanical movement markers are systole markers of heart chambers which comprise atrial systole markers and ventricular systole markers;
   wherein the atrial systole markers and ventricular systole markers are graphically represented as bars that are displayed in a time relationship with the ECG information; and
   wherein a length of each atrial systole marker and ventricular systole marker indicates an atrial systolic duration and a ventricular systolic duration, respectively;
   wherein each bar is parallel to a time axis, each bar corresponding to an atrial systole is displayed in a first line parallel to the time axis, each bar corresponding to a ventricular systole is displayed in a second line parallel to the time axis, and two ends of each bar respectively correspond to an end-diastolic time point and an end-systolic time point;
   wherein a distance is formed between the bars representing the atrial systole and the ventricular systole of a heartbeat, and wherein a connection line is displayed connecting the end-diastolic time points of two bars.

18. The method of claim 17, wherein, the mechanical movement markers of the atrium and the ventricle and the ECG information are displayed on a display device along a same time line.

19. The method of claim 17, wherein the generating mechanical movement markers of an atrium and a ventricle according to the echocardiography images comprises:
   obtaining trajectories of edges of the atrium and the ventricle according to the echocardiography images;
   obtaining inner diameters of the atrium and the ventricle according to the trajectories of the edges of the atrium and the ventricle;
   obtaining characteristics time points of movement cycles of the atrium and the ventricle according to the inner diameters;
   determining systoles of the atrium and the ventricle according to the characteristics time points of the movement cycles; and
   obtaining the mechanical movement markers according to the systoles of the atrium and the ventricle.

20. The method of claim 17, wherein the echocardiography images are M mode ultrasound images.

* * * * *